United States Patent [19]
Young

[11] Patent Number: 5,833,600
[45] Date of Patent: Nov. 10, 1998

[54] METHOD OF DIAGNOSING AMYGDALA RELATED TRANSITORY DISORDERS AND TREATMENT THEREOF

[76] Inventor: Robert B. Young, 3036 Rte. 89, Seneca Falls, N.Y. 13148

[21] Appl. No.: 906,080

[22] Filed: Aug. 5, 1997

Related U.S. Application Data

[62] Division of Ser. No. 517,317, Aug. 21, 1995, Pat. No. 5,707,334.

[51] Int. Cl.$^6$ .................................................. A61B 10/00
[52] U.S. Cl. .............................................. 600/300; 600/9
[58] Field of Search ................................ 600/9–15, 300; 128/897, 898

[56] References Cited

U.S. PATENT DOCUMENTS

| | | |
|---|---|---|
| 4,134,395 | 1/1979 | Davis ...................................... 600/9 X |
| 4,940,453 | 7/1990 | Cadwell . |
| 4,994,015 | 2/1991 | Cadwell ................................... 600/13 |
| 5,085,627 | 2/1992 | Fedorov et al. . |
| 5,116,304 | 5/1992 | Cadwell . |
| 5,176,145 | 1/1993 | Ryback et al. . |
| 5,215,086 | 6/1993 | Terry, Jr. et al. . |
| 5,342,410 | 8/1994 | Braverman . |
| 5,441,495 | 8/1995 | Liboff et al. . |
| 5,496,258 | 3/1996 | Anninos et al. . |

FOREIGN PATENT DOCUMENTS

| | | |
|---|---|---|
| 725671 | 6/1980 | U.S.S.R. . |
| 1274693 | 1/1997 | U.S.S.R. . |

OTHER PUBLICATIONS

A. Eisen, Cortical and percipheral nerve magnetic stimulation, Meth. Clin. Neurophys, Jul. 1992,3:65–84.

A. Pascual–Leone et al., Induction of speech arrest and counting errors with rapid–rate transcranial magnetic stimulation, Neurology 1991 May, 41:697–702.

R. Ryback & E. Gardner, Limbic system dysrhythmia: A diagnostic electroencephalogram procedure utilizing procaine activation, J. Neuropsych Mar. 1991 Summer, 3(3):321–329.

*Primary Examiner*—John P. Lacyk
*Assistant Examiner*—Samuel Gilbert
*Attorney, Agent, or Firm*—Kenyon & Kenyon

[57] ABSTRACT

The invention relates to a method for diagnosing and treating Amygdala Related Transitory Disorders, comprising selecting a patient who has symptoms suggesting ARTD, stimulating said patient's amygdala with a magnetic field, and determining whether said stimulus with a magnetic field is capable of inducing or aggravating symptoms of ARTD. Additional embodiments comprise a method to determine the lowest dose of an anticonvulsant that will effectively control ARTD, and methods of using electromagnetic stimuli to treat ARTD by interfering with kindling or desensitizing the amygdala.

8 Claims, 2 Drawing Sheets

METHOD OF DIAGNOSING AMYGDALA RELATED TRANSITORY DISORDERS AND TREATMENT THEREOF

This application is a division of application Ser. No. 08/7517,317, filed on Aug. 21 1995, now U.S. Pat. No. 5,707,334.

FIELD OF THE INVENTION

The present invention generally relates to the treatment of neurological disorders. In particular, it relates to the use of electromagnetic stimulation to diagnose and treat neuropsychiatric disorders. More specifically, it relates to methods for diagnosing and treating patients afflicted with Amygdala Related Transitory Disorders.

BACKGROUND OF THE INVENTION

The limbic system (comprising the amygdala, hypothalamus, anterior thalamic nuclei, gyrus cynguli, hippocampus, temporal lobe and their interconnections), in particular the amygdala, have been implicated in a variety of neuropsychiatric disorders. Patients suffering from Amygdala Related Transitory Disorders ("ARTD") exhibit a wide range of seemingly unrelated symptoms, which include (but are not limited to): mood changes (e.g., anxieties, dominating thoughts, impaired alertness, fatigue, hallucinations, irritability, low threshold for frustration, chronic and recurring depressions, panic attacks of varying intensity); thirst and appetite disorders; bodily pain, especially focal, bilateral or generalized headaches, including migraine headaches; muscle tension; addictions to alcohol, cigarettes or drugs and bulimia; writing, speech, and learning disabilities; perceptual dysfunctions (i.e., problems in integrating sensory—visual or auditory input); paranoid thinking; peripheral neuropathies (e.g., paresthesia or hypoesthesis in one or more extremities, usually episodic); seizure-like phenomena (e.g., blackouts, trances or impaired consciousness, myoclonic twitches); self-destructive behavior (including cutting, burning, biting self, hitting self or walls).

Little is known of the physiological basis for symptoms of ARTD. In addition to any possible permanent neurological damage of the hypothalamus limbic temporal lobe and brain stem areas, it is believed that ARTD may be characterized by periodic, episodic or paroxysmal dysfunctions in the amygdala. Typically, the dysfunction manifests itself as a group of symptoms, often occurring in periodic bursts. Different ARTDs may map to different positions in the limbic systems.

The symptoms of ARTD can be effectively treated with anticonvulsants. However, ARTD is often misdiagnosed and therefore mistreated.

A principal reason for the difficulty in diagnosing ARTD is the wide variation of symptoms: a defined set of observable symptoms may characterize ARTD in one patient, whereas a different set of symptoms may predominate in another ARTD patient. For example, one patient may become very fearful when suffering from an ARTD, while another patient may experience obsessive thoughts or hallucinations, while still a third patient may engage in stalking, alcoholism, violent behavior, etc.

Furthermore, while ARTD is almost always manifested by more than one symptom or sign, be it psychiatric or neurological, current treatments tend to focus on and treat only the predominant or most incapacitating one. For example, a physician may focus on depression and thus fail to recognize other symptoms of ARTD such as obsessions or excessive thirst. This may mistakenly lead to treatment with antidepressants, instead of to a diagnosis of ARTD and treatment with anti-convulsants. Without the use of the anticonvulsant medication, the use of the antidepressant or neuroleptic medication is usually ineffective or may actually exacerbate (especially with antidepressants) the ARTD.

Clearly, there is need for a method of reliably diagnosing ARTD. There is also need for safer treatment.

In the past, the interrelationship between certain disorders and neural activity has been determined by activating specific neural centers by a variety of means, mainly chemical stimuli and electrical impulses.

For example, neurologists have successfully used electrical stimuli to map the regions of the cortex that are involved in specific cognitive functions (e.g., spatial recognition, color perception, etc.) and to form the basis for, or confirm, clinical diagnoses. The Food and Drug Administration (FDA) has approved a number of Cranial Electrotherapy Stimulation (CES) devices for the treatment of anxiety, insomnia and depression.

U.S. Pat. No. 5,342,410 discloses a method and apparatus for increasing electrical brain activity, thereby decreasing cravings for addictive substances. The invention comprises a cranial electrotherapy stimulation device which generates a substantially periodic current waveform having a frequency approximately between 50 and 300 Hz, a current amplitude in the range of 0 to 400 mA, a voltage of approximately 40–60 volts, a pulse width in the range of 0.20 to 2 milliseconds and a duty cycle of about 20%. The patient is stimulated with the device for between 20 minutes and two hours. Such stimulation results in an increase in the amplitude of P300 waves in the brain, which in turn reportedly results in a decrease in cravings for alcohol and drugs. Patent No. 1274693 from the Soviet Union claims a method for treating depressions wherein an anode is positioned on the occipital-mastoidal region (behind the ear) and a cathode is positioned on the frontal region. The sensory threshold is gaged by increasing current intensity until the individual first senses the current. An electric current with a pulse repetition rate ranging from 1 to 100 Hz is then applied to the right or the left hemisphere of the brain for 7 to 15 minutes once every 2–3 days (8–10 times altogether). Treatment of the right side of the brain is recommended to treat emotional disorders characterized by prevalence of anxiety and treatment of the left side of the brain is recommended to treat anguish and apathy.

U.S. Pat. No. 5,215,086 discloses methods and an apparatus for treating and controlling migraine by selectively stimulating a patient's vagus nerve, using an implantable neuro-stimulating device. The signal is a pulse waveform designed to desynchronize the patient's electroencephalogram (EEG) if paroxysmal activity is detected in the EEG, or to synchronize the EEG if low voltage fast wave activity is detected. Alternatively, the application of the stimulating signal to the vagus nerve may be initiated manually by the patient upon recognition of the onset of a migraine attack.

Patent No. 725671 from the Soviet Union discloses a method for treating depressions with electrical stimuli, wherein an anode is placed on the palm of a hand and a cathode is placed on the lower third of the forearm of the same arm, and electric pulses are applied with a voltage 2–3 times the sensitivity threshold at a pulse repetition rate from 10 to 100 Hz. The treatment lasts for 2 to 10 minutes with intervals of 3 to 7 days. The treatment is repeated once every 3 to 4 months once or twice to prevent the relapse of depressions.

Certain electrical stimuli can produce self-maintaining independent seizure foci. This phenomenon, known as "kindling", is optimally produced by intra-cortical stimulation at stimulation rates of 50/s. A rate of less than 3/s will generally not suffice. Trains of repetitive stimuli are often required. Repetition rates of less than 3/s are reportedly safe.

However, there are significant counterindications to the use of electrical currents. Electrical currents can be painful, and their application often requires the use of anesthetics. The sensitivity threshold mainly depends on the electrical conductance properties of the skin. This threshold may vary substantially during the course of treatment of one and the same individual, depending on his emotional condition. It may also vary as a function of a number of subjective factors (e.g., fear of pain). Moreover, the usefulness of methods that rely on electrical stimulation is limited by its inability to penetrate into deep peripheral nerves, nerve plexi, and subcranial nerves. Finally, in chronic electrical stimulation of the brain using electrodes, reversible injury to the blood-brain barrier may occur if the charge exceeds 45 $\mu$C and neuronal injury occurred as charged densities increased from 40–400 $\mu$C/cm2 per phase.

The intravenous administration of the anesthetic procaine has been reported to suppress neocortical structures while selectively stimulating the limbic system. Procaine induces patients to experience the symptoms or ARTD; this induction is called "kindling". The effect of procaine on the limbic system has been likened to the treadmill stress test in cardiology. The treadmill stimulates the heart muscle, unmasks abnormal cardiac patterns and is used to evaluate the effect of drugs on the abnormal patterns. Similarly, procaine has been used to unmask limbic electroencephalogram dysrhythmia, to occasionally recreate the concomitant behavior disorder, and to evaluate pharmacological treatment.

U.S. Pat. No. 5,176,145 to Ryback and Gardner and also Ryback and Gardner, J. Neuropsychiatry 3: 321–329 (1991) disclose and claim a method for diagnosing whether a patient suffers from limbic system dysrhythmia ("LSD"), involving studying electroencephalogram patterns for focal abnormalities in the temporal parietal areas. If there are none, the patient is administered a local anaesthetic, procaine, and the electroencephalogram is evaluated for omega band activity (30–50 Hz). A patient exhibiting either focal abnormalities in the temporal-parietal areas on the standard electroencephalogram or, after procaine, exhibiting omega band activity of at least about three times the baseline voltage above normal and exhibiting symptoms in at least four groups of twelve groups of defined symptoms is diagnosed as having LSD and being capable of treatment by administering an anticonvulsant medication.

A time-varying (pulsed) magnetic field applied to a tissue capable of conducting electrical currents will result in an induced current as though the current had been applied via electrodes. The induced current will flow in planes parallel to the plane of the inducing magnetic coil, and in opposite directions. Good conductors, e.g., neurons, blood, and cerebrospinal fluid, will have larger currents than skin, fat, or bone, which present high resistance to electrical currents.

The brain has a relatively high conductivity, whereas the electrical resistance of the skull is 8 to 15 times greater than that of soft tissue. While bone structures and cavities would limit currents generated with electrodes, they would not significantly attenuate a magnetic field. Thus, magnetic fields may induce currents in deeper tissues and over broader ranges than an electrical stimulus produced by electrodes.

Accordingly, transcranial magnetic stimulation has been used instead of electrical currents to stimulate or detectably alter neural activities. See, e.g., Eisen, Meth. Clin. Neurophys. 3: 65–84 (1992). Pascual-Leone et al., Neurology 41: 697 (1991) reported that stimulation rates of up to 25 Hz for ten seconds using a coil held flat on the scalp induced speech arrest in patients without detectable damage to the brain tissue.

Magnetic stimulators may not substitute for electrical stimuli in all cases. For example, it has been reported that cardiac muscle cannot be stimulated with a magnetic coil. Eisen at 66.

SUMMARY OF THE INVENTION

The ability to reasonably predict whether a patient would be successfully treated by a particular course of medication is of great importance; an incorrect diagnosis could not only result in an ineffective treatment but in one that might be harmful to the patient. Accordingly, it is an object of this invention to provide a diagnostic method for ARTD that has a very high probability of success and is relatively easy and safe to carry out.

It is a principal object of the present invention to detect and treat ARTD by selectively stimulating nerve activity within the amygdala, by exposing a patient to subcranial magnetic fields using a magnetic neurostimulator device, in order to induce at least one but preferably more than one symptom from a group of defined symptoms of ARTD.

In one embodiment, a magnetic coil (or coils), movably joined to and exposed at the top surface of a mouthpiece, is (are) held in place against the nasopharynx of a patient. The coil(s) is (are) held in place, for example, by reversibly affixing it (them) to the mouthpiece, and having the patient "clamp down" on the mouthpiece assembly comprising the coil and the mouthpiece without biting through any component of this assembly. The mouthpiece is preferably a wax or plastic mold of the patient's mouth. The coil or coils may be reversibly affixed to different positions on the mouthpiece.

The magnetic stimulation is preferably a "sub-threshold stimulation", i.e., of a magnitude insufficient to elicit either the behavioral or brain wave manifestations of an ARTD in non-ARTD control subjects. If kindling is observed after a number of repetitive sub threshold stimuli, then the patient is diagnosed as having an ARTD. Of equal importance, the absence of symptoms following such stimulation indicates that the cause of the patient's symptoms is not an ARTD, and the patient should not be treated for such disorder.

Once the diagnostic embodiment of the invention indicates that the patient is suffering from an ARTD, the physician can prescribe an appropriate treatment. For example, anticonvulsants that counteract kindling can be prescribed for patients who manifest several symptoms or signs concurrently. In another embodiment of the present invention, a physician can determine the lowest dose of the anticonvulsant that will effectively control ARTD.

In other embodiments of the invention, electromagnetic forces such as rapid rate subcranial stimulation may be used to interfere with kindling or desensitize certain areas in the brain.

DETAILED DESCRIPTION OF THE INVENTION

Figure 1:
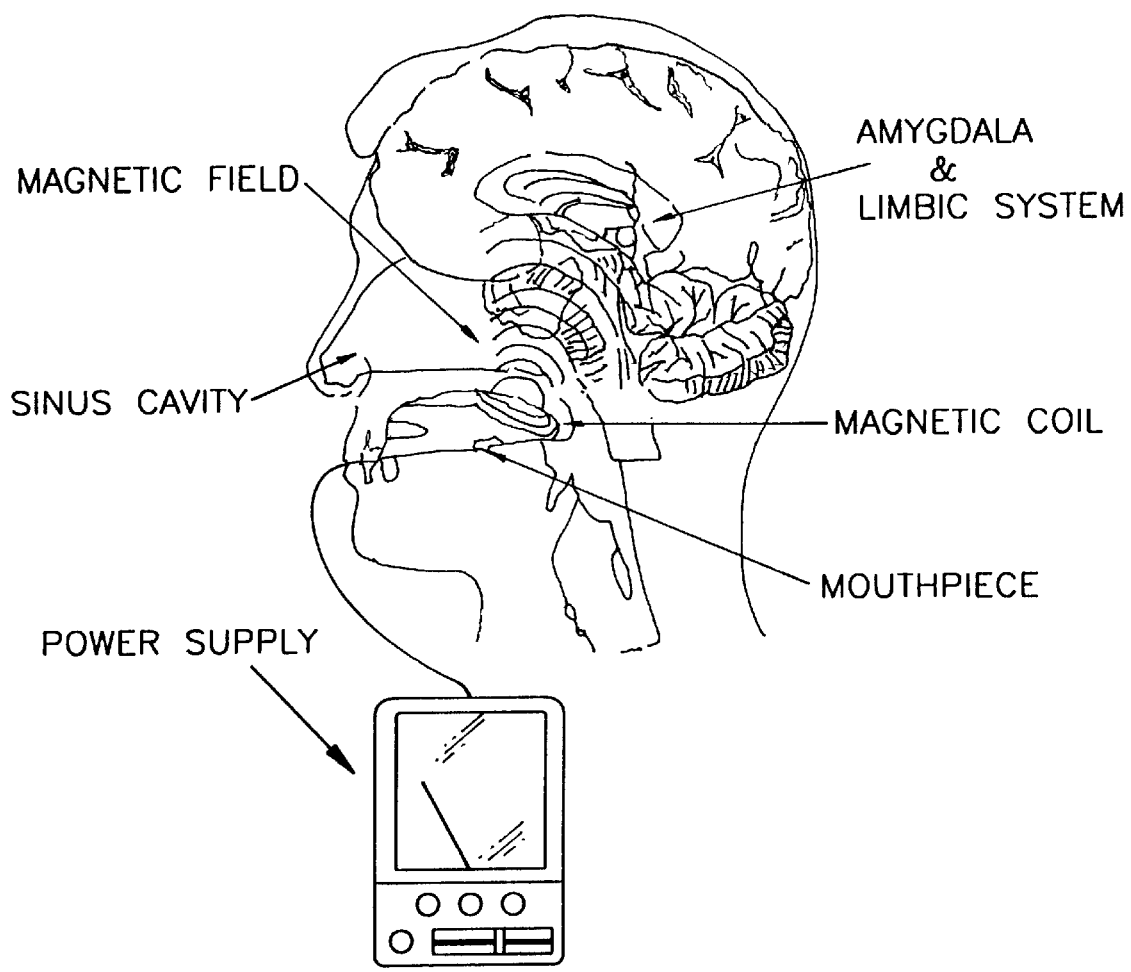
FIG. 1 is a diagram of the basic components of a neurostimulator and their interrelationship.

The various publications referenced herein are incorporated by reference in this application in order to more fully describe the state of the art to which the present invention pertains. All technical and scientific terms used herein, unless otherwise defined, are intended to have the same meaning as commonly understood by one of ordinary skill in the art, with the proviso that the terms used herein are not intended to be limiting of the invention. The term "amygdala" encompasses not only the amygdala proper, but also other components of the limbic system. Although the invention focuses preferentially on human patients exhibiting symptoms of ARTD, the invention also encompasses the analysis of asymptomatic relatives of persons exhibiting these symptoms who may be "at risk" for developing ARTD, and the treatment of other mammals having similar symptoms.

The published methods for treating neural disorders by stimulating neural activity relied on electrical stimulation or, in the case of the method for diagnosing limbic disorders disclosed in U.S. Pat. No. 5,176,145, procaine administration, both of which have a number of significant drawbacks. On the one hand, localized electrical stimulation is severely limited by its inability to penetrate into deep peripheral nerves, nerve plexi, and subcranial nerves. Deeper penetration may be obtained by increasing the current, but this approximates electroshock treatment, which is painful and may cause grand mal convulsions. Also, medication and general anesthesia are required with stronger currents. On the other hand, intravenous procaine administration is invasive and its effects are systemic rather than localized, with a known potential for side-effects.

The present invention utilizes subcranial electromagnetic fields to stimulate the amygdala/limbic system. It is less invasive and simpler to carry out than either electrical stimulation or procaine. It affords better penetration and more specific targeting of regions of the brain. It offers the advantages of electroconvulsive therapy (ECT) (e.g., potential for deliberate controlled stimulus of localized tissues), but not its disadvantages. It is painless and easier and safer than ECT. Selective magnetic probing of the limbic system by evoking the patients own symptoms is more reliable than the general kindling induced by intravenous procaine. The patient need not be anesthetized or worry about pain, as with ECT. This assures better patient acceptance of the treatment.

In fact the patient is usually fully aware and capable of describing the effects of the neurostimulation as it takes place. This enormously simplifies the task of correlating field strength and orientation to neuropsychiatric phenomena, and greatly facilitates the fine structural mapping of the locus of the physical dysfunctions that give rise to an ARTD.

While magnetic neurostimulation has been reported in the literature to study neurological functions, its use to diagnose and treat ARTD has neither been suggested nor disclosed in the prior art.

Procedurally, the invention comprises the steps of:
a. selecting a patient who has symptoms of ARTD and/or whose EEG indicates abnormal omega band activity three times baseline upon subcranial magnetic stimulation (SMS),
b. stimulating said patient's amygdala with a magnetic field, and
c. determining whether said stimulus with a magnetic field induces symptoms of ARTD.

A. Selecting a Patient

To select a patient, the physician performs a symptom inventory. In such a symptom inventory, the physician investigates the patient's past history with respect to: moods, anxieties, dominating thoughts, thirst, appetite, impaired alertness, fatigue, pain, hallucinations, irritability, writing, speech, frustration, etc. If the patient reports symptoms in these categories, then the patient may be suffering from ARTD, especially if the reported group of symptoms occur in periodic bursts.

1. Questionnaire

The most efficient way to perform the symptom inventory is through a questionnaire. The following is a model questionnaire used by the inventor:

MOOD
Do you experience depressions or mood swings?
Could the depressions start suddenly?
Do you have crying spells?
Are your depressions short lived?
Would they come and go within the same day or last for just a few days?
Is there a reason to become depressed?
Are they triggered by certain things?
Are they totally unpredictable or do you feel them coming on?
If so what do you feel?

ANXIETY
Do you have panic attacks, a sudden overwhelming fear?
Do you have phobias, or fears from certain things or situations?
Do you anticipate anxiety?
Do you have anxiety in social situations?

THOUGHTS
Do you suffer from obsessive thoughts, recurrent or unwanted thoughts?
Do you dwell on things, keep thinking about things of the past?
Do you ever have racing thoughts, that is, do your thoughts ever go 100 mph or you can't put them still?
Do these racing thoughts ever keep you up at night?

DRINKING
Are you a thirsty person?
Do you drink more fluids than the average person, any fluid, water, soda, not necessarily alcohol?
Do you drink a lot of alcohol?
Are you a volume drinker?
Do you drink beer?
Do you drink mostly in the evening?
Do you drink in order to sleep?
Do you ever experience drinking binges?
A sudden urge to drink, even at night?
Is your thirst easily quenched by drinking?

FOOD
Do you have a good morning appetite?
Do you feel nauseous in the morning?
Does your appetite improve as the day progresses?
Do you suddenly loose appetite while you eat?
Do you suddenly have a craving for food? Is this irresistible to the point you just have to eat, i.e. impulsive eating or food-binging?
Is your appetite ever not satiated by eating?
Does it occur at night, wake you up and make you go to the refrigerator?

SLEEP
Do you have trouble sleeping?
Do you have trouble falling asleep?
Do you have trouble staying asleep?

Do you have to pace at night?
Do you have vivid dreams?
Do you have jerky movements in bed?
Do you get up tired in the morning?
Do you have trouble with yawning, do you yawn a lot during the day?
Do you grind your teeth at night?
Do you sleepwalk or experience night terrors?
COGNITION
Do you ever feel clouded or dazed, half asleep, or with a decreased awareness? In other words, do you ever feel that you are not fully alert?
Do you feel this in the morning?
Does it clear as the day progresses?
At what time are you fully awake?
Do you sometimes bump into things, for example, run into a doorjamb?
Are you at your best in the evening? Are you sharp then?
Do you daydream a lot? When does it occur, in the morning, or in the evening?
Do you have trouble with your memory or concentration?
Are you a night person, do you think more clearly in the evening?
PAIN
Do you have headaches or migraines?
Do you have a sudden pain in the pit of your stomach and would that pain go upwards, in the chest, to your neck?
Do you have sudden pain in your throat?
FATIGUE
Do you sometimes feel tired or exhausted? Suddenly and for no reason?
Do you wake up tired in the morning?
HALLUCINATIONS
Visual: Do you ever see black dots, lightning, stardust, small objects or people?
Auditory: Do you have ringing in the ears, or do you hear bells ringing? or a buzzing sound?
Do you hear voices or hold conversations within yourself? or a humming sound?
Olfactory: Do you ever smell anything that's not there? Do you ever smell anything unusual, something burning, burning rubber, corpses? Do you ever have no smell at all?
Taste/Gustatory: Do you ever have no taste? Do you everhave an unusual taste, such as metallic or foul taste?
IRRITABILITY
Visual: Does strong light ever bother you or irritate you, such as sunlight, T.V., fluorescent lights?
Does bright light hurt?
Do you have to wear sunglasses, use shades excessively?
Can you tolerate light some days and other days not?
Auditory: Do loud noises bother you? Does it hurt or irritate you? Can you tolerate noises some days and other days not? Can you hear things at a great distance?
WRITING
Do you ever write too much or a lot, more than usual?
Do you ever write a lot of poems, letters to important people?
SPEECH
Do you ever talk too much?
Do people tell you to stop talking?
Are you sometimes speechless?
Do you ever feel you have nothing to say and would justremain silent as if there were no need to talk?
Do you ever stutter?
Do you ever have trouble finding your words?
Do you find it difficult to terminate a conversation?
FRUSTRATION Do you ever become intolerant, for no reason?
Do you ever become very frustrated, unable to tolerate it?
Would you then be very angry and lash out?
Do you ever experience strong negative feelings, even hatred, when you feel there may be no real reason for that?
Would you say that overall this anger, frustration, intolerance, etc. are not really you, that you are basically a different person?
SEXUAL
Do your symptoms get worse towards your periods?
Do you have an increased or decreased sexual drive?
Is there some degree of promiscuity?
PERSONALITY
Do you feel you may have several personalities?
Are you a routine person? Do you feel it is difficult to change or adapt?
Do you feel you are a unique person, an outsider, or someone who doesn't blend with the crowd?
Do you have times you loose self confidence, yet at other moments you may be quite self confident?
Are you overly sensitive at times, even to the point of becoming paranoid?
Are you very concerned with what's right and wrong in life or with injustices in the world?
Do you dread going to work in the morning but once you get started you are more or less OK?
Do you find yourself clinging to people?
PERCEPTIONS
Do you ever experience cold or hot flashes?
Do you ever experience numbness in your arms, legs, body?
Do you experience deja vu or deja entendu, already heard? Do you feel you have a 6th sense, that is, do you have premonitions or can make predictions?
2. Electroencephalogram The results of the questionnaire are based on the patient's subjective answers, and may be subject to error because of the patient's misperception, miscommunication, or misrepresentation, or the physician's bias or misunderstanding. An electroencephalogram may provide an objective criterion in the diagnosis of ARTD. The presence of either focal abnormalities in the temporal-parietal areas in a standard electroencephalogram or of omega band activity of at least about three times the normal baseline voltage (as described in U.S. Pat. No. 5,176,145) may bolster an initial diagnosis of ARTD that results from the above-defined symptoms inventory.

The measure of objectivity provided by EEG analysis may prove useful in ruling out hypochondriasis and malingering. It may further confirm cases of, for example, irresistible impulse in homicide cases, which then could plead an insanity defense on a more scientific basis, bypassing the subjectivity of neuropsychiatric experts.

Patients having an abnormal EEG (including focal abnormalities) should not be tested. These patients typically would suffer from epilepsy.

B. Magnetic Stimulation

Once a patient is identified as apparently suffering from ARTD, his amygdala is probed with a subcranial magnetic stimulator. The goal is to identify and focus on the anatomical region that is prone to kindling and is causing the patients' neuropsychiatric symptoms and/or signs. This region will become the target of symptom suppression in a later treatment phase.

Figure 2A:
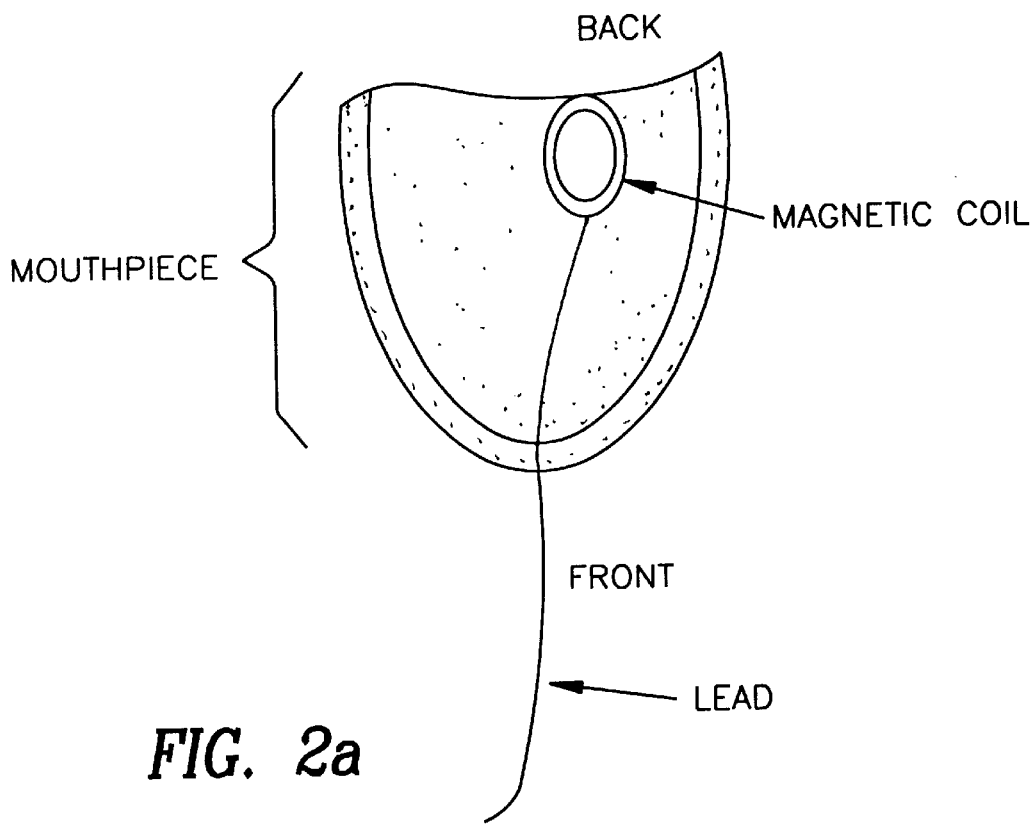
FIGS. 2a and 2b illustrate the mouthpiece and one possible placement of a magnetic coil.
Figure 2B:
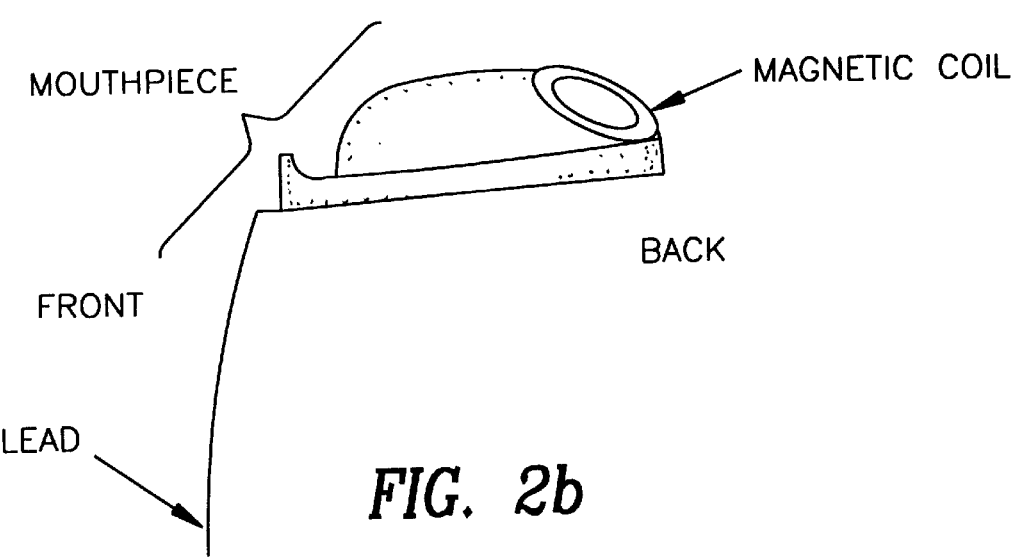

A block diagram of the basic components of a neurostimulator and their interrelationship is illustrated in FIG. 1. The main components are a power source connected to a means, usually a coil, of generating a magnetic field, and also means for controlling the strength, shape, duration and direction of the magnetic field. Further details of a preferred embodiment involving a mouthpiece and the lead/magnetic coil system are shown in FIGS. 2a and 2b. The neurostimulator device is usually external to the body, but a portion of the circuitry (e.g., coils and associated leads) may be optionally implanted.

The following is a brief summary of the functions of the main elements of a preferred magnetic neurostimulator.

The neurostimulator utilizes a power supply which determines the peak charging voltage (and thus its intensity) and also limits the rate at which the stimulator charges (and thus its repetition rate). It is important that the power supply be designed so that failure modes will not significantly increase either of these parameters.

The power supply is preferably equipped with a microprocessor, a computer and associated software for adjustment of parameters and control of communication between the generator and other standard electrical and electronic components for generating and modulating the desired magnetic field or indicating states of the device. In conjunction with its microprocessor-based logic and control circuitry, the stimulus generator circuitry may include detection circuitry for sensing an event indicative of an abnormality that triggers an automatic delivery of the stimulating signal. For example, specific characteristics of the patient's EEG could trigger the therapy.

Magnetic stimulators produce magnetic fields by pulsing an intensive current through a suitable coil. This current is generated when a high value capacitor is suddenly discharged by a switching device (thyristor).

When the magnetic coil and the capacitor are connected through a solid state switch, the energy moves rapidly from the capacitor to the coil creating a magnetic field, the strength of which is measured in Teslas (T; one T=10,000 gauss). A magnetic stimulator may deliver pulses of between 1–10 T. Most experimentation for peripheral and central stimulation has used field strengths of about 1 to about 2.5 T.

Thus, a magnetic stimulator's electrical circuit preferably comprises an inductor (stimulating coil) and, because it is necessary to obtain a rapid increase in excitation coil current and to deliver a high peak current to the coil, an energy storage capacitor with a very low equivalent series resistance (ESR). The capacitor provides the energy of stimulation.

The capacitors deliver large currents for short durations. The intensity of stimulation is proportional to the voltage, which is set by the power supply, and to the square root of the capacitance. For current magnetic stimulators, the duration is generally fixed by the capacitors and the coil inductance, and so generally only the amplitude of the stimulus is varied.

The capacitance is set by the charge energy allocated, approximately 500 J being wanted in many applications. This would require 4000 mfd at 500 V or 250 mfd at 2000 V. The latter combination is preferable because the much lower currents involved not only allow finer gauge and therefore more compact coils, but system efficiency is also greatly improved.

The capacitor is discharged into the coil by a solid state switch. Typically, the peak current is in the kiloampere range. The resulting pulse of current induced into the tissue is of short duration, typically in the fractional multi-second range. The voltage drop across these parts decreases the stimulus by approximately 0.5%. Changes with temperature or age have little effect on stimulus intensity. The main requirement of the switches is surviving the high surge requirements.

The coil transfers the energy back to the capacitor, and if the switch remains closed, the energy moves again from the capacitor to the coil, back and forth, until it is entirely consumed by resistive losses.

In a prototypical stimulator, a current pulse of up to 5000 A (peak current) is passed through a flat 45 mH copper coil of 10 cm diameter. The peak magnetic field strength is approximately 1–3 T and the duration of the induced currentpulse is approximately 100 ms. The energy storage capacitor bank is charged to 4 kv and discharged into the coil (2 kV is adequate for superficial nerves) resulting in a brief magnetic field, peaking at 160 ms. The maximum frequency of stimulation is once every 3 seconds. The power can be turned up until the desired response has been obtained.

The production of heat by the coil is a limiting factor of the rate of repetitive pulses. The coil is designed for minimum resistance with enough inductance (i.e., amount that the coil resists the changing current measured in Henries) to protect the switching elements from over-current. Computer modeling shows a 0.7–1.0% change in the effectiveness of the stimulation with a 100% increase in coil inductance.

An underdamped condition is preferred in magnetic field stimulators, to keep the resistance low and to favor low heating in the coil. In this condition the current is oscillatory and the induced current or stimulus pulse resembles a damped cosine wave. The output is a damped oscillation lasting about 800 $\mu S$.

Coil design is key to providing localized stimulation, as design affects the shape and intensity of the magnetic field. Circular coils and double circular ("butterfly") coils have been used, but any geometric shape (oval, ellipsoid, triangular, square, figure-eight, parallel wires, etc.) or combination of geometric shapes is possible, depending on the desired shape, strength and application. The magnetic field intensity and the shape of the field can be easily measured and mapped, if desired.

A preferred embodiment in this invention is a magnetic coil shaped as an ellipse measuring about 7 cm wide and 9 cm long. The elliptical shape generates a narrower, more focused magnetic field.

At present, a number of neurostimulators suitable for use in embodiments of the present invention are commercially available. For example, the Cadwell laboratories, Inc. High Speed Magnetic Stimulator features rapid firing capability and adjustable intensity. Maximum stimulation rate is 25 Hz at 100% intensity and 50 Hz at 50% intensity. It generates a magnetic field of up to 2.2 T. In addition, Dantec markets its Mag Pro stimulator with a built-in trigger source offering a train duration from about 0.2 to about 10 seconds with repetition rates of about 5–30 pulses per second. Manual operation and external trigger is provided, as well as the capability of selecting a biphasic or monophasic stimulation waveform, and the current direction can be reversed.

C. Use of Magnetic Neurostimulator

To stimulate excitable tissue, a threshold current needs to be induced in that tissue, generally sufficient to reduce the transmembrane potential by approximately 30%. Nerves respond to an appropriate stimulus by depolarizing. The appropriate time scale of the stimulus is relative to the neuron's ability to pump sodium ions in an attempt to maintain equilibrium, typically 100–300 ms. A charge density of 1–2 $\mu C/cm2$ is sufficient to depolarize myelinated nerves. For a convenient electrical stimulator this would be 10 mA * 100 µS. Increasing either the duration or the amplitude of the stimulator will increase the effectiveness of the stimulation.

For magnetic stimulators the duration is fixed by the capacitors and the coil inductance. Typically, the induced current is only 1/100,000 the size of the inducing current. The stimulus is 1000 times smaller than that used for ECT and the energy is about 1 million times smaller.

Up to 460 J of energy is needed to depolarize the brain. This large amount is required because the brain is almost transparent to magnetic fields.

Which region of the brain is stimulated depends on the strength, shape and direction of the magnetic field. These parameters are strongly influenced by the shape, current flowing through, and placement of the coil.

A magnetic field that originates outside the skull would likely stimulate cortical structures a well as the amygdala. Thus, preferably the magnetic coils are positioned subcranially such that they are adjacent to the amygdala. More preferably, they are positioned adjacent to the nasopharynx or the posterior region of the soft palate.

In one embodiment the magnetic field strength is about 0.1 to about 4 Tesla, the magnetic field is administered in trains of pulses, wherein each train lasts from about 5 seconds to about 10 minutes, each train comprising 1–20 second pulses, with an interval of 1–20 seconds between pulses.

Consistency of coil positioning and orientation relative to the targeted structures are essential for reproducible results. This is especially true where the physician wishes to stimulate only a particular region of the amygdala or the limbic system. For the sake of accuracy and reproducibility, it is preferable to control the position and angle of the coil. This is preferably achieved by affixing the coil to a stable solid support. It is further preferable that this affixation be reversible. In other words, it is preferable that the physician or patient be able to fix the coil to a given position at will, and also change this position at will. A preferred embodiment for such a support is a mouth piece molded after the patient's mouth, as illustrated in FIGS. 1 and 2. Such a custom-molded piece has the double advantage that it fits snugly and comfortably in the patient's mouth, without slippage. It also makes it easier to position the coil. The mouthpiece may by made of a semisoft material capable of holding its shape, such as soft dental wax, or it may be made of non-toxic plastic. The plastic mouthpiece may be made by first making a template of a semisoft material such as dental wax, for example by directly applying the soft wax into the patient's mouth, as the patient firmly bites into the wax. The wax template may then be used to make a mold patterned after the template. The mold thus made may be filled with a polymerizable or solidifiable material such as plastic.

In an alternate embodiment, the lead wire is threaded through the nasal passage of a patient, an the coil is positioned adjacent to the nasopharynx. The position and angle of the coil prior to magnetic stimulation are monitored with an imaging device, such as ultrasound or X-rays.

The stimulus generator is designed, implemented and programmed to deliver a selectively patterned stimulating signal to modulate limbic activity in a manner designed to treat the specific neuropsychiatric disorder of interest. The magnetic stimulus is applied continuously, periodically or intermittently.

The diagnostic stimulation starts off at low stimulation rate, say 1 to 3 pulses per second at low power, and a magnetic field strength of 1 to 2 T, lasting for about 5–30 seconds. The stimulation rate, field strength, and duration are increased until magnetically induced kindling is achieved, either as reported by the patient, or by measuring the omega band activity on an EEG display. Kindling may be optimized by progressively changing the position and angle of the coil, for example, by moving the probe from left to right about a frontal-posterior axis. Regions from different depths of the limbic system may be scanned, the penetration depth being controlled by increasing the magnetic field strength.

The patient himself may participate by varying the depth and direction of the field by using hand controls while the stimulating coil is in his mouth. The patient could not only control direction and depth of the field but also, for example, the rate of stimulation which would trigger his own symptoms or exacerbate them. The patient would thus be able to find his own kindling-sensitive spot within the limbic system.

If upon this diagnostic stimulation, either 1) a concurrent EEG monitoring discloses Omega band activity of three times the baseline value or 2) the patient experiences symptoms or signs which are typical of his condition, then the patient suffers from ARTD. He can then be treated with anticonvulsants and/or rapid rate subcranial magnetic stimulation (RRSMS). If RRSMS is administered in the treatment phase, it will be desirable to stimulate at a rapid rate that area of the limbic system that was activated in the diagnostic stimulation test. Maintaining the same angles and penetration depth, stimulation will be provided at a rapid rate of about 25 pulses per second in 10 second trains for about 2 minutes twice a week for a month.

Once an optimal stimulation is obtained, subsequent treatment would utilize the same position, angle, field strength, pulse rate, and duration.

The magnetic stimulation is preferably given to the patient at a level insufficient to elicit either the behavioral or brain wave manifestations of an ARTD in non-ARTD control subjects, hereinafter a "sub-threshold" stimulation. If kindling is observed after a number of repetitive sub-threshold stimuli, then the patient is diagnosed as having an ARTD.

The diagnostic method of the present invention makes it possible to distinguish a category of patients who are most likely to show positive responses to treatment with an anticonvulsant medication or RRSMS.

D. Treatment of ARTD

Patients who meet the above-described criteria are diagnosed as having ARTD. They are then treated by administration of an anticonvulsant medication such as Tegretol (carbamazepine), Depakene or Depakote (valproic acid), or Klonopin (clonazepam), alone or in combination with other medications, as appropriate (e.g., antidepressants or neuroleptic medication).

The anticonvulsant medication is generally orally administered. Recommended dosages are listed in the Physician's Desk Reference, 1995 Edition, Medical Economics Company, or they may directly obtained from the manufacturer of the anticonvulsant medication.

ARTD patients who are treated with anticonvulsants on a regular basis exhibit a decrease in the frequency and intensity of the symptoms characteristic for this particular patient. the patient's response to stimulation, both above and below the threshold decline, i.e., fewer symptoms are perceived nd the EEG is normalized.

The present invention not only provides a method for identifying patients who can benefit from anti-convulsant therapy, but it also provides methods for determining the most effective dose of a given medication for a specific patient. Dosages can then be tailored to the individual tolerances of a particular patient, and dosage can be reduced or increased from the prescribed dosage as needed (e.g., 25–200% of recommended dose.) The present invention also provides a method for ascertaining which among alternative medications works best for a given patient.

Accordingly, in one embodiment of the present invention, a physician determines the lowest dose of the anticonvulsant that will effectively control an ARTD. To do so, a patient is administered a predetermined dose of an anticonvulsant, preferably the recommended dose, and then her amygdala is probed with the magnetic neurostimulator, with the coil positioned and the magnetic field parameters set to values previously determined to induce an ARTD in that patient. If the patient does not exhibit kindling following magnetic stimulation of the amygdala, then the dose is progressively reduced, until the minimum dosage that determines kindling is ascertained. If on the other hand the patient exhibits kindling at the initial dose following magnetic stimulation of the amygdala, then the patient is administered progressively higher doses until the medication effectively inhibits kindling.

The invention is useful also to determine whether and to what extent a patient may have become habituated to the medication. After a patient with such a disorder is receiving a dose of anticonvulsant for a while or if other medications are also taken that would affect bio availability of the anticonvulsant, such test could be used to determine proper dosage.

Treatment with anticonvulsants may be contra-indicated in certain patients. Anticonvulsant medications typically have undesirable side effects such as depression of bone marrow proliferation, with a subsequent drop in white blood cell count. Also, the anticonvulsant Tegretol is teratogenic, and it is not suitable for use with pregnant women or in children. In these instances, a less invasive, safer treatment is indicated. Rapid Rate Subcranial Magnetic Simulation (RRSMS) is such a treatment.

Once the region of the limbic system has been identified that undergoes kindling in response to magnetic neurostimulation, patients are treated with Rapid Rate Subcranial Magnetic Simulation (RRSMS) as an alternative to anticonvulsants. The RRSMS is delivered by placing the magnetic coil in the same position and orientation, and exposing the patient to a magnetic field having the same strength, shape, direction, train frequency and depth, as that shown to induce kindling in that patient. The frequency of the magnetic stimulation is the major parameter to be adjusted when passing from the diagnostic probing phase to the therapeutic RRSMS phase. Repeated kindling over extended periods desensitizes the patient and allays the ARTD.

E. Other Uses

The present invention contemplates that localized and selective stimulation of certain areas within the brain by magnetic stimulation will enhance or decrease the concentration and/or effect of neurotransmitters such as acetylcholine, dopamine, endorphins, norepinephrine or serotonin. Their levels in or outside the limbic system will be manipulated when desired. It is desirable, for example, to increase acetylcholine in the nucleus basalis to improve an Alzheimer's condition. Or it would be desirable to increase Dopamine in the substantia nigra of Parkinson's patients. Or it would be desirable to increase endorphin levels in pain control (such as was done with TENS).

Magnetic stimulation of the limbic system is also useful to combine with and enhance the effects of neuropsychiatric medications. By activating the corresponding centers, it may also promote relaxation and induce sleep. Magnetic stimulation may also be used to treat suicidal ideation or homicidal ideation. Also recidivism of compulsive rapists, serial murderers, even arsonists, could be curtailed significantly.

In addition, the methods of this invention permit a precise determination of structure-function correlations in affected areas of the limbic system. The magnetic stimulation as taught herein allows the physician to pinpoint with some accuracy the locus of the limbic system that correlates with a given patient's ARTD. This locus may then be studied in greater detail (e.g., a subsequent post mortem examination of the brain tissues would focus on the affected area and allow for more specific research than is now possible.

It will be apparent to those skilled in the field from the foregoing description that variations and modifications of the above embodiments, methods and techniques may be made without departing from the true spirit and scope of the invention. For example, the use of transplantable coils and a portable power source is fully contemplated by the invention. The invention also fully contemplates an embodiment wherein the patient himself decides when to apply the magnetic stimulus (e.g., when he feels the onset of an ARTD).

What is claimed is:

1. A method for determining whether a patient has an Amygdala Related Transitory Disorder (ARTD) and is susceptible to being treated by administration of an anticonvulsant medication or by Rapid Rate Subcranial Magnetic Stimulation (RRSMS), comprising the steps of:

(a) selecting a patient who has at least one symptom suggestive of ARTD;

(b) stimulating said patient's amygdala with a magnetic field; and (c) determining whether said stimulus with a magnetic field is capable of inducing or aggravating at least one symptom of ARTD; and (d) determining whether the patient has an ARTD based upon the induction or aggravation of at least one symptom of ARTD caused by the magnetic stimulus.

2. A method according to claim 1, wherein said patient is selected by determining whether said patient exhibits at least one symptom selected from the group consisting of mood change, panic attacks, rage, headaches, addictive states, learning disability, paranoid episodes or thinking, peripheral neuropathic signs, seizure-like phenomena, self-destructive behavior, autoimmune-endocrine disorders and antidepressant stimulant response.

3. A method according to claim 1, wherein said magnetic stimulus is administered by:

(a) subcranially placing one or more coils capable of mediating the formation of a localized electromagnetic field; and (b) generating a localized electromagnetic field.

4. A method according to claim 3, wherein the coils are placed adjacent to the patient nasopharynx.

5. A method according to claim 3, wherein the coils are placed adjacent to the patient's soft palate.

6. A method according to claim 5, wherein the coils are placed adjacent to the patient's soft palate by movably affixing them to a mouthpiece, and introducing the mouthpiece in the patient's mouth.

7. A method according to claim 3, wherein a multiplicity of magnetic stimuli of defined strength and duration are administered at defined intervals.

8. A method according to claim 7, wherein
   (a) the magnetic field strength is about 0.1 to about 4 Tesla;
   (b) the magnetic field is administered in trains of pulses, wherein each train lasts from about 5 seconds to about 10 minutes; and
   (c) the field is administered in 1–20 second pulses, with an interval of 1–20 seconds between pulses.

* * * * *